United States Patent
Dodel

(10) Patent No.: US 11,471,336 B2
(45) Date of Patent: Oct. 18, 2022

(54) DRESSING

(71) Applicant: Lohmann & Rauscher GmbH & Co. KG, Neuwied (DE)

(72) Inventor: Kirsten Dodel, Neuwied (DE)

(73) Assignee: Lohmann & Rauscher GmbH & Co. KG, Neuwied (DE)

( * ) Notice: Subject to any disclaimer, the term of this patent is extended or adjusted under 35 U.S.C. 154(b) by 279 days.

(21) Appl. No.: 16/639,726

(22) PCT Filed: Jul. 3, 2018

(86) PCT No.: PCT/EP2018/067954
§ 371 (c)(1),
(2) Date: Feb. 17, 2020

(87) PCT Pub. No.: WO2019/034322
PCT Pub. Date: Feb. 21, 2019

(65) Prior Publication Data
US 2021/0128363 A1 May 6, 2021

(30) Foreign Application Priority Data
Aug. 18, 2017 (DE) .......................... 102017118964.5

(51) Int. Cl.
*A61F 13/02* (2006.01)
*A61F 13/00* (2006.01)

(52) U.S. Cl.
CPC .. *A61F 13/023* (2013.01); *A61F 2013/00821* (2013.01); *A61F 2013/00829* (2013.01)

(58) Field of Classification Search
CPC .............. A61F 13/023; A61F 13/00055; A61F 13/00059; A61F 2013/00153; A61F 2013/00182; A61F 2013/00846; A61F 2013/00851; A61F 13/02; A61F 2013/00868; A61L 15/58; A61L 15/26
See application file for complete search history.

(56) References Cited

U.S. PATENT DOCUMENTS 5,628,724 A    5/1997   DeBusk et al.

FOREIGN PATENT DOCUMENTS

| EP | 1683502 A1 | 7/2006 |
| WO | WO 94/21207 A2 | 9/1994 |

OTHER PUBLICATIONS

International Preliminary Report on Patentability dated Nov. 7, 2019 for International Patent Application No. PCT/EP2018/067954, 21 pages.

*Primary Examiner* — Ophelia A Hawthorne
(74) *Attorney, Agent, or Firm* — Schwabe, Williamson & Wyatt, P.C.

(57) ABSTRACT

A dressing for application to human or animal skin and/or to medical devices, comprising a fixing web provided with an adhesive on a fixing surface, covering means removably attached to the fixing surface, and support means connected to the covering means and removably attached to an outer surface of the fixing web facing away from the fixing surface, wherein the outer surface has an exposed shaping surface which is at least partially surrounded by the support means.

11 Claims, 2 Drawing Sheets

Fig. 2
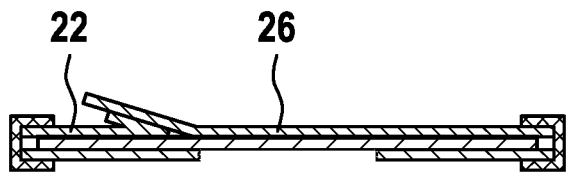
a)
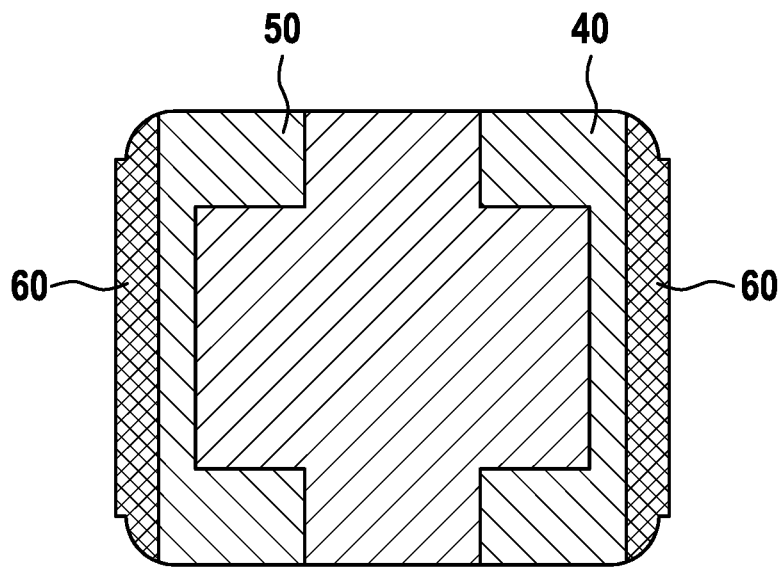
b)
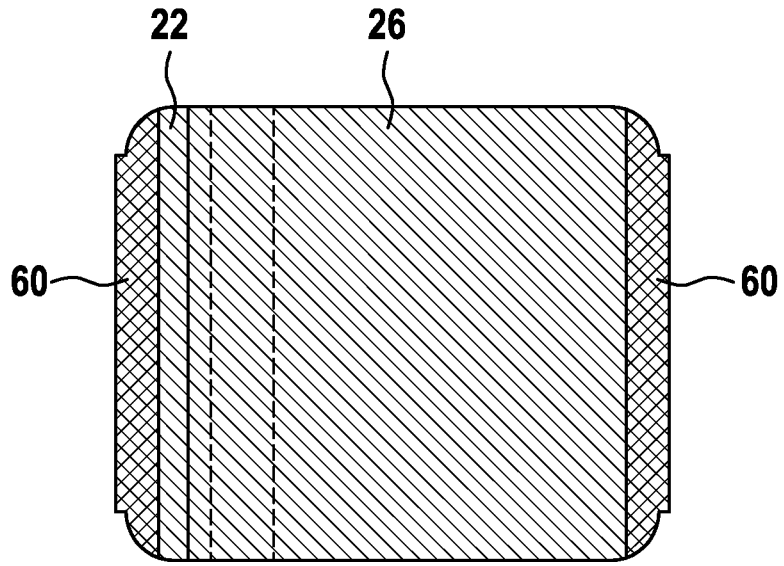
c)

DRESSING

CROSS REFERENCE TO RELATED APPLICATION

The present application is a 35 U.S.C. § 371 national phase entry application of, and claims priority to, International Patent Application No. PCT/EP2018/067954, filed Jul. 3, 2018, which claims priority to German Patent Application No. 102017118964.5, filed Aug. 18, 2017, the disclosures of which are hereby incorporated by reference in their entirety for all purposes.

BACKGROUND

The invention relates to a dressing for application to human or animal skin and/or to medical devices, covering means removably attached to the fixing surface, and support means connected to the covering means and removably attached to an outer surface of the fixing web as specified in independent claims 1 and 5.

Such dressings implemented in the form of film dressings or film plasters are described for instance in WO 98/25559. In the known dressings, the fixing web is implemented as a thin, optionally transparent polymer foil with an adhesive layer disposed on its fixing surface. Before use of the dressing, the adhesive layer or adhesive itself is completely covered with a covering means, for example silicone paper. In this instance, the covering means may comprise several parts, each individual part of the covering means being provided with a gripping aid, for example in the form of an edge that is folded back over itself. To apply such a dressing, the individual parts of the covering means are peeled off the fixing surface, which may then be fixed to human or animal skin using the adhesive.

In the known dressings, a support means removably attached to the outer surface of the fixing web facing away from the fixing surface, in the form of support films removably attached to the outer surface, contributes to avoiding that the fixing surface folds over on itself during application and sticks to itself, making the dressing unusable.

In the known dressings, the individual parts of the covering means are connected to the support film covering the outer surface. They can be used as gripping aids for the support film when the support film is to be removed from the fixing web after application of the dressing or plaster.

The connection between the support film and covering means may also be obtained with a support film and individual parts of the covering means formed integrally with each other. Moreover, WO 98/25559 also describes an arrangement in which the individual parts of the covering means are connected to the support film by film hinges. The disclosure of WO 98/25559 regarding the connection between the support film and covering means is hereby expressly incorporated by reference.

With known dressings, it has been shown that in practical use, in particular in order to fix medical devices such as catheters or cannulas in place, the fixing web can sometimes undesirably peel off human or animal skin to which it should be fixed. Furthermore, it has been shown that the application itself is only possible with great difficulty.

DE 10 2005 003 391 A1 corresponding to EP 1 683 502 A1 describes a plaster optimized for machine production. This plaster may be produced with a minimum number of process steps. For that purpose, a support material is applied on a continuous fixing web and is stamped out to form support frames for the individual plasters. The rest of the support material is removed. After separating individual plasters with their respective fixing webs, cover materials and support frames from the continuous web, the individual plasters are sealed into a foil or paper wrapper. In many cases, use of such plasters can also lead to undesirable removal of the fixing web from the skin and to problems during application. Similar dressings are disclosed in WO 94/21207 and U.S. Pat. No. 5,628,724.

DE 10 2012 223 399 A1 mentions a wound dressing that can be cut to size, having the characteristics of the preamble of claim 1. In this known dressing, the support means may comprise a plurality of gripping areas distributed over its outer periphery. This facilitates both the removal of the support means after cutting the wound dressing to size and the removal of the covering means.

In consideration of the prior-art problems described above, it is an object of the invention to provide a dressing which, on the one hand, is easy to apply and, on the other hand, remains securely adhered to the skin.

This object is achieved according to the invention by a further development of the known dressings as specified in the appended claims.

In the context of the present invention, the support means at least partially surrounds the exposed shaping surface when there are two points on the shaping-surface-facing edge of the support means which are linked together with a straight line lying inside the shaping surface.

This solution relies on the knowledge that the problems arising when using dressings as known from WO 98/25559 are primarily attributable to the stiffening action of the support film covering the complete outer surface of the fixing web in the known dressings as this stiffening action hampers shaping of the fixing web to the skin, cannulas, catheters and/or other medical devices. This not only creates an obstruction during application of the dressing itself, but also leads to the fixing web failing to completely cover the skin, catheter and/or cannula after application because the stiffening support film prevents attachment of the fixing web to particular contours with smaller radii of curvature. This can cause a premature removal of the fixing web from the skin, cannulas or catheters.

In the dressings according to the invention, the outer surface is not completely covered by a support film. Instead, an exposed shaping surface is created between the support means, where the outer surface of the fixing web is not covered. This shaping surface of the fixing web may be freely shaped to skin surfaces, cannula surfaces or catheter surfaces without being impaired by the support means to achieve a secure attachment. Incidentally, the support means offers an effective solution to avoid the fixing surface sticking to itself. This provides for a simple application of the dressing while ensuring a secure attachment. This achievement brought about by the invention is also essentially supported by the fact that the support means is connected to the covering means in such a way that the covering means forms a gripping aid after application of the dressing to the skin and/or medical instruments so that the support means is removable from the outer surface of the fixing web without such removal of the support means from the fixing web leading to a poorer attachment of the fixing web, as is the case with the plasters disclosed in DE 10 2005 003 391 A1 which are indeed easy to machine produce but are difficult to apply.

Similarly to the dressings known from WO 98/25559, the covering means of the dressings according to the invention may also have two, three or more foil or paper-like covering strips which together form a complete cover for the fixing surface while being individually removable from the fixing surface.

The covering strip may be more easily removed from the fixing surface when at least one covering strip has an edge that is folded back over itself to form a gripping aid. When the covering means comprises two covering strips, both covering strips may have edges folded back over themselves and extending in opposite directions from a parting line separating both covering strips.

To achieve an all-over covering of the fixing surface with the covering means, it has however proved useful to have an edge of one of the covering strips overlapping the folded back edge of a neighbouring covering strip so as to avoid exposing the parting line between the covering strips. With regard to the design of individual covering strips, reference is made to the disclosure of WO 98/25559, which is hereby expressly incorporated by reference in this matter. The present invention also encompasses the use of one-piece support means which preferably completely surround the shaping surface.

In the invention, the support means may be formed integrally as one continuous frame.

According to another aspect of the invention, which may be combined with the above-mentioned aspect of the invention, the support means may have two, three or more supporting parts which are independently removable from the outer surface, of which one at least partially overlaps a covering strip in a projection direction which is perpendicular to the fixing surface, wherein said at least one supporting part is connected to said covering strip such that, after removal from the fixing surface, the covering strip forms a gripping aid for the supporting part connected therewith, to facilitate removal of the supporting dressing.

In this aspect of the invention, it is possible to first detach a covering strip from the fixing surface, apply the fixing web with the thus exposed area of the fixing surface to the skin or a medical device, then also remove from the fixing web the part of the support means connected with the removed covering strip, with the use of the covering strip as a gripping aid, and then shape the exposed area of the fixing web in an appropriate manner, before the remaining covering strips and supporting parts are detached from the fixing web. In this regard, it has proved particularly useful that the projection of the supporting part in the projection direction perpendicular to the fixing surface does not totally cover the covering strip, such that after detaching the covering strip and removing the supporting part, there remains an exposed shaping surface, in the vicinity of said supporting part, which is easy to shape to the contours of the skin and/or medical instruments after removal of the covering strip.

As stated above, the covering strip may be formed integrally with the support means or supporting part, as in a dressing according to WO 98/25559. Additionally or alternatively, the covering strip may also, in a similar way to the known dressings, be connected to the support means or a supporting part by a film hinge running around an edge of the fixing surface.

A sufficient shaping surface may be provided in the dressings according to the invention when the shaping surface occupies more than 20%, preferably more than 30%, more preferably 40% or more of the outer surface, so that a corresponding surface portion is not covered by the support means.

In order to achieve a balanced compromise between appropriate shapeability and sufficient stability of the dressing during application, it has proved useful that the shaping surface occupies less than 90%, preferably less than 80%, more preferably 70% or less of the outer surface. In a particularly preferred embodiment of the invention, the proportion of the shaping surface on the total outer surface of the fixing web is approximately 60%.

When the projection of the supporting part does not totally cover the covering strip connected therewith, it has proved useful, to achieve sufficient stability, that the supporting part covers more than 10%, preferably more than 15% of the outer surface, and the covering strip connected therewith covers 20% or more of the fixing surface. It is possible to obtain sufficient shapeability when the supporting part covers less than 30%, preferably less than 20% of the outer surface, and the covering strip connected therewith covers 50% or less, preferably 40% or less of the fixing surface.

A greater variability in the dressings according to the invention is obtained when the covering strips cover different surface portions of the fixing surface. For example, a covering strip may cover approximately 40% of the fixing surface, while another covering strip may cover approximately 60% of the fixing surface. In some cases, it can be useful to first expose the smaller fixing surface area and to apply it to the skin or medical devices before exposing the larger fixing surface area in order to complete the application. In other cases, it may be useful to proceed in reverse order.

According to the invention, it is particularly preferred that a supporting part is approximately U-shaped and has two exterior legs connected to each other by a connecting leg, wherein the exterior edge of the connecting leg runs along an edge of the fixing web and is connected with a covering strip particularly via a reinforcing strip running around this edge. When the fixing web is generally rectangular, the exterior edges of the exterior leg may run approximately along the edges of the fixing web. The surface exposed between the exterior legs and connecting legs then forms at least a portion of the shaping surface of the fixing web.

Further, it has proved particularly advantageous to have support means having two approximately U-shaped supporting parts, wherein the ends of the exterior legs extending away from the connecting legs of individual supporting parts face each other to form a frame for the shaping surface.

The application of such dressings may be further simplified when a space is left free between the mutually opposite ends of the exterior legs, said space being preferably somewhat smaller than the length of the exterior legs of the supporting parts.

As mentioned above with reference to known dressings, it has proved particularly useful that the fixing web is, at least in sections, transparent, particularly in the area of the shaping surface, particularly in the form of a polymer foil.

As used within the present description, the term "fixing web" denotes a peripherally contoured fabric having, for example, a square, rectangular, oval, circular or polygonal contour.

BRIEF DESCRIPTION OF THE DRAWINGS

The invention is described more fully below, with reference to the drawings illustrating all details which are essential to the invention and are not explained further in the description. In the accompanying drawings:

FIG. 2 shows a dressing according to a second embodiment of the invention.

FIG. 1a) shows a cross-section across a dressing of the invention, along a sectional plane running perpendicular to the fixing web. FIG. 1b) shows a top view of a boundary surface of the dressing as per FIG. 1a), provided with a support means. FIG. 1c) shows a top view of the boundary surface of the dressing as per FIG. 1a), provided with a covering means.

DETAILED DESCRIPTION

Figure 1:
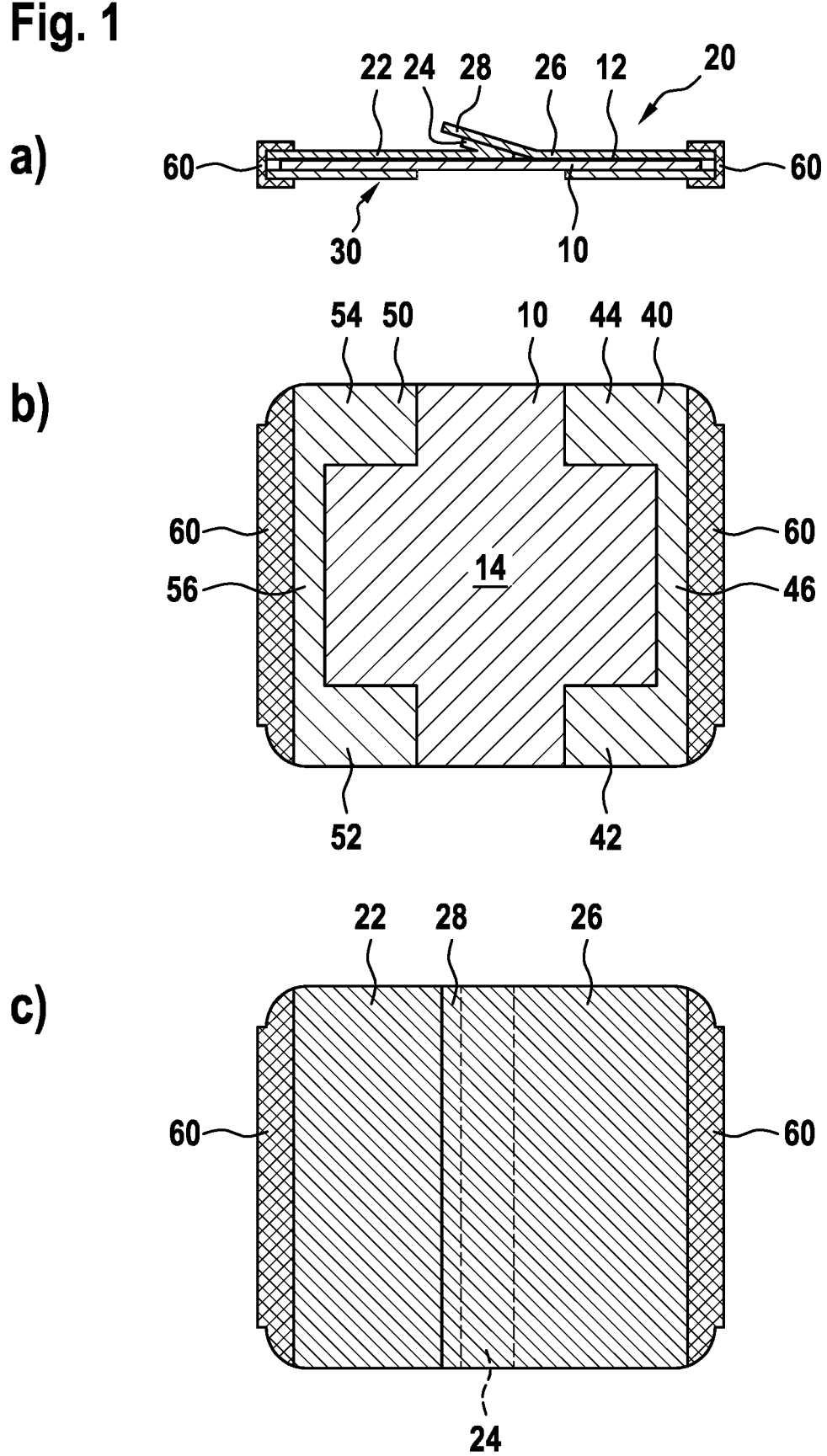
FIG. 1 shows a dressing according to a first embodiment of the invention.

The dressing illustrated in FIG. 1 comprises an approximately rectangular fixing web with rounded corners (see FIGS. 1b) and 1c)). A fixing surface of the fixing web 10 is provided with an adhesive 12. The adhesive 12 is covered with a two-piece covering means 20.

The boundary surface of the fixing web 10 which faces away from the adhesive 12 is provided with a support means generally denoted with reference numeral 30.

The covering means 20 comprises two approximately rectangular covering strips 22 and 26 with parallel edges. Edge 24 of covering strip 22 facing towards covering strip 26 is folded back over itself. Edge 28 of covering strip 26 facing towards covering strip 22 overlaps edge 24 of covering strip 22 which is folded back over itself. This leads to complete coverage of the fixing surface, or adhesives 12 applied thereon, and simultaneously, through edges 24 and 28, provides a gripping aid for the covering strips.

The edges of covering strips 22 and 26 which are facing away from overlapping edges 24 and 28 are connected with support means 30 using hinge-forming reinforcing strips 60. These reinforcing strips overlap boundary surfaces of covering strips 22 and 26 facing away from the fixing web on the one hand, and boundary surfaces of support means 30 facing away from the fixing web on the other hand, and run around opposite edges of fixing web 10.

As is clearly visible in FIG. 1b), support means 30 is a two-part member, wherein supporting part 40 is connected with covering strip 26 using a reinforcing strip, whereas supporting part 50 is connected with covering strip 22 using another reinforcing strip. Both supporting parts are approximately U-shaped, having two respective exterior legs 42, 44 and 52, 54 connected pairwise through respective connecting legs 46 and 56. Connecting legs 46 and 56 are parallel to the edges of the fixing web which are overlapped by reinforcing strips 60, whereas exterior legs 42, 44 and 52, 54 are perpendicular to these edges.

As is clearly visible in FIG. 1b), supporting parts 40 and 50 form a frame for a shaping surface 14 disposed on the boundary surface of the fixing web 10 which is facing away from fixing surface 12 and is uncovered by the support means. A space is left free between the mutually opposite ends of exterior legs 42, 44 and 52, 54 of supporting parts 40 and 50 to facilitate the shaping of the shaping surface to the contours of medical instruments and/or human or animal skin. As is visible in FIG. 1c), fixing surface 12 of fixing web 10 is completely covered by covering strips 22 and 26.

To apply the dressing illustrated in FIG. 1, covering strips 22 and 26 are detached simultaneously or sequentially from fixing surface 12 of fixing web 10 using gripping aids 24 and 28. They remain connected with the support means or support parts 40 and 50 through reinforcing strips 60. During this process, the assembly remains stable, even after detaching covering strips 22 and 26 from fixing surface 12. This simultaneously provides a shaping surface 14 which is not covered by supporting parts 40 and 50 and facilitates the shaping of the fixing web.

Once the fixing web has been shaped, supporting parts 40 and 50 may be detached from the boundary surface of fixing web 10 facing away from the fixing surface, wherein covering strips 22 and 26 may be used as gripping aids. The dressing may thus be applied in a simple and secure manner.

In the embodiment of the invention illustrated in FIG. 1, covering strips 22 and 26 cover approximately similar surface portions of fixing surface 12 of fixing web 10. The support means is disposed substantially in mirror-symmetry to a surface bisectrix of the fixing web's outer surface.

The embodiment of the invention illustrated in FIG. 2 differs substantially from the embodiment of FIG. 1 in that different surface portions of the fixing surface are covered by individual covering strips 22 and 26. Similarly to the embodiment illustrated in FIG. 1, the parting line separating the covering strips is substantially parallel to connecting legs 46 and 56 of supporting parts 40 and 50. This embodiment allows for an increased variability during application of the dressing because a smaller surface portion of the fixing surface or a larger surface portion of the fixing surface may be exposed first depending on the requirements for the application site.

The invention is not limited to the above embodiments illustrated for explanatory purposes, but is intended to include the use of dressings having three or more supporting parts, wherein the covering means may be produced as a one-piece member in some cases. In other embodiments of the invention, the outer surface of the fixing web may be totally covered by the support means. In such embodiments, it should be noted that the support means is to be produced as a multi-piece member. In other embodiments of the invention, the support means may be formed as an integral or continuous frame and may completely surround the shaping surface.

The fixing web may, for example, be made of transparent polyurethane. The covering strips may consist of covering paper. Other embodiments are also possible, such as those in which the covering strips are formed integrally with the supporting parts.

The invention claimed is:

1. A dressing, comprising a fixing web provided with an adhesive on a fixing surface, a means for covering removably attached to the fixing surface, and a means for supporting connected to the means for covering and removably attached to an outer surface of the fixing web facing away from the fixing surface, characterized in that the means for covering has two or more foil or paper shaped covering strips, wherein at least one covering strip has an edge that is folded back over itself to form a gripping aid and an edge of one of the covering strips overlaps the edge that is folded back over itself of a neighboring covering strip and in that the means for supporting has two or more supporting parts which are independently removable from the outer surface, of which at least one at least partially overlaps a covering strip in a projection direction which is perpendicular to the fixing surface, wherein said at least one supporting part is connected to said covering strip such that, after removal from the fixing surface, the covering strip forms a gripping aid for the supporting part connected therewith, wherein at least one covering strip is formed integrally with the means for supporting, in particular with a supporting part of the means for supporting and/or at least one covering strip is connected to the means for supporting, in particular to the supporting part of the means for supporting, by a film hinge running around an edge of the fixing surface.

2. The dressing according to claim 1, characterized in that the supporting part is approximately U-shaped and has two exterior legs connected to each other by a connecting leg, wherein an exterior edge of the connecting leg runs along an edge of the fixing web and is connected with a covering strip particularly via a reinforcing strip running around this edge.

3. The dressing according to claim 2, characterized in that the means for supporting has two U-shaped supporting parts, wherein ends of the exterior legs extending away from the connecting legs of the supporting parts face each other to form a frame for the shaping surface.

4. The dressing according to claim 2, wherein a space is left free between respective mutually opposite ends of the exterior legs.

5. The dressing according to claim 1, characterized in that the shaping surface occupies more than 20 of the outer surface.

6. The dressing according to claim 1, characterized in that the shaping surface occupies less than 90%, of the outer surface.

7. The dressing according to claim 1, characterized in that the supporting part covers more than 10%, of the fixing surface.

8. The dressing according to claim 1, characterized in that the supporting part covers less than 30% of the outer surface, and the covering strip connected therewith covers 50% or less of the fixing surface.

9. The dressing according to claim 1, characterized in that the fixing web is, at least in sections, transparent, in the area of the shaping surface.

10. The dressing according to claim 1, characterized in that the fixing web is substantially rectangular, with rounded corners, oval, circular and/or polygonal.

11. A dressing for application to human or animal skin and/or to medical devices, comprising a fixing web provided with an adhesive on a fixing surface, a means for covering removably attached to the fixing surface, and a means for supporting connected to the means for covering and removably attached to an outer surface of the fixing web facing away from the fixing surface, wherein the outer surface has an exposed shaping surface which is at least partially surrounded by the means for supporting, characterized in that the means for covering comprises two or more foil or paper shaped covering strips, wherein at least one covering strip has an edge that is folded back over itself to form a gripping aid and an edge of one of the covering strips overlaps the edge that is folded back over itself of a neighboring covering strip, and in that at least one covering strip is formed integrally with the means for supporting, with a supporting part of the means for supporting and/or at least one covering strip is connected to the means for supporting, to the supporting part of the means for supporting, by a film hinge running around an edge of the fixing surface.

* * * * *

UNITED STATES PATENT AND TRADEMARK OFFICE
CERTIFICATE OF CORRECTION

PATENT NO. : 11,471,336 B2
APPLICATION NO. : 16/639726
DATED : October 18, 2022
INVENTOR(S) : Kirsten Dodel It is certified that error appears in the above-identified patent and that said Letters Patent is hereby corrected as shown below:

In the Claims

Column 6, Line 47, Claim 1:
"... paper shaped..." should read -- paper-shaped --

Column 7, Line 7, Claim 7:
"... the connecting legs..." should read -- connecting legs --

Column 8, Lines 12-14, Claim 11:
"... surrounded by the means for supporting, characterized in that the means for covering comprises two or more..." should read -- surrounded by the means for supporting, characterized in that the means for covering comprises two or more --

Line 14, Claim 11:
"... paper shaped..." should read -- paper-shaped --

Signed and Sealed this
Twentieth Day of August, 2024

Katherine Kelly Vidal
*Director of the United States Patent and Trademark Office*